United States Patent
Mamiya et al.

(10) Patent No.: US 9,071,040 B2
(45) Date of Patent: Jun. 30, 2015

(54) ION GENERATOR

(75) Inventors: Toshio Mamiya, Osaka (JP); Masato Urushisaki, Osaka (JP); Takashi Nakabayashi, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 235 days.

(21) Appl. No.: 13/812,955

(22) PCT Filed: Jun. 10, 2011

(86) PCT No.: PCT/JP2011/063316
§ 371 (c)(1),
(2), (4) Date: Jan. 29, 2013

(87) PCT Pub. No.: WO2012/014577
PCT Pub. Date: Feb. 2, 2012

(65) Prior Publication Data
US 2013/0126749 A1   May 23, 2013

(30) Foreign Application Priority Data

Jul. 30, 2010   (JP) .................... 2010-171281

(51) Int. Cl.
*H01T 23/00* (2006.01)
*F24F 3/16* (2006.01)
*A61L 9/22* (2006.01)

(52) U.S. Cl.
CPC ............ *H01T 23/00* (2013.01); *F24F 3/166* (2013.01); *F24F 2003/1682* (2013.01); *A61L 9/22* (2013.01)

(58) Field of Classification Search
CPC ....................................... H01T 23/00

USPC ............. 250/423 R; 422/121, 22; 96/15
See application file for complete search history.

(56) References Cited

U.S. PATENT DOCUMENTS

| 4,333,123 A | 6/1982 | Moulden |
| 6,221,160 B1 | 4/2001 | Lin |
| 2004/0130271 A1 | 7/2004 | Sekoguchi et al. |
| 2004/0253417 A1 | 12/2004 | Sekoguchi et al. |
| 2007/0107452 A1 | 5/2007 | Kim et al. |
| 2011/0155922 A1 | 6/2011 | Funabiki et al. |
| 2011/0257870 A1 | 10/2011 | Nishioka et al. |
| 2012/0014840 A1 | 1/2012 | Hanai et al. |
| 2012/0085921 A1 | 4/2012 | Nishida |
| 2013/0095000 A1 | 4/2013 | Yamamoto et al. |
| 2013/0126749 A1 | 5/2013 | Mamiya et al. |

FOREIGN PATENT DOCUMENTS

| CN | 101175510 A | 5/2008 |
| JP | 09-213493 A | 8/1997 |

(Continued)

OTHER PUBLICATIONS

Official Communication issued in International Patent Application No. PCT/JP2011/063316, mailed on Sep. 13, 2011.

(Continued)

*Primary Examiner* — Robert A Hopkins
(74) *Attorney, Agent, or Firm* — Keating & Bennett, LLP (57) ABSTRACT

A partition is formed between an ion generating unit at the windward side and an ion generating unit at the leeward side, so that the amount of airflow to pass through the ion generating unit at the windward side will become more in comparison to the amount of airflow to pass through the ion generating unit at the leeward side.

10 Claims, 8 Drawing Sheets

(56) References Cited

FOREIGN PATENT DOCUMENTS

| | | | |
|---|---|---|---|
| JP | 2001-035686 A | 2/2001 | |
| JP | 2002-319472 A | 10/2002 | |
| JP | 2003-047651 A | 2/2003 | |
| JP | 2003-161494 A | 6/2003 | |
| JP | 2009-36408 A | 2/2009 | |
| JP | 2010-055960 A | 3/2010 | |
| JP | 2010051398 A | * | 3/2010 |
| JP | 2010-80425 A | 4/2010 | |
| JP | 2010-080431 A | 4/2010 | |
| JP | 2010-118351 A | 5/2010 | |
| JP | 2011-33293 A | 2/2011 | |
| JP | 2011-60705 A | 3/2011 | |
| WO | 2010/146966 A1 | 12/2010 | |

OTHER PUBLICATIONS

Kataoka; "Ion Generator"; U.S. Appl. No. 14/238,410, filed Feb. 11, 2014.

* cited by examiner

ION GENERATOR

TECHNICAL FIELD

The present invention relates to an ion generator provided with an ion generating device that emits positive and negative ions into air.

BACKGROUND ART

As a method of creating a comfortable environment in a living space, there have generally been used air conditioners for purifying air in the living space. Examples of such air conditioners include one that maintains the temperature and humidity in the space at a comfortable level, and also there is an air purifier having a filter or the like for purifying air. If such apparatuses further incorporate an ion generating device that emits ions into air, it is possible to have ions emitted together with purified air or temperature- and humidity-conditioned air. In particular, increase in the amount of negative ions can be expected to give people a relaxation effect.

Thus, if an air conditioner incorporating an air purifying device is further provided with an ion generating device, it is possible to provide a comfortable air environment, and simultaneously, to expect emitted negative ions to give people a relaxation effect.

Furthermore, by making the ion generating device emit positive ions as well as negative ions, it is possible to obtain, in addition to the above effects, effects of inactivating germs, molds, odors and the like by, for example, killing, decomposing, or removing them. In such an ion generating device, by, for example, corona discharge performed in the air, equal amounts of $H^+(H_2O)_m$ (m represents any natural number) and $O_2^-(H_2O)_n$ (n represents any natural number) are emitted as positive and negative ions, respectively. The emitted positive and negative ions adhere to and cover up molds, germs, and viruses floating in the air, and, thanks to the action of hydroxyl radical (.OH), a radical species, which is generated as a result of reaction occurring there, it is possible to inactivate the molds, germs, and the like floating in the air. Examples of inventions related to such an ion generating device have already been disclosed in Patent Literatures 1, 2, and 3 listed below.

CITATION LIST

Patent Literature

Patent Literature 1: JP-A-2003-047651
Patent Literature 2: JP-A-2002-319472
Patent Literature 3: JP-A-2010-055960

SUMMARY OF INVENTION

Technical Problem

According to the ion generators disclosed in Patent Literatures 1 and 2, positive ions and negative ions are alternately generated by applying AC voltage to a single electrode portion provided to perform corona discharge. In contrast, in the ion generator disclosed in Patent Literature 3, there are provided two separate electrode portions, one dedicated to generate negative ions and the other dedicated to generate positive ions.

In a conventional ion generator that incorporates an ion generator where positive and negative ions are separately generated, a positive ion generating unit and a negative ion generating unit are arranged in a direction perpendicular to a flow of air sent from a blower as described in Patent Literature 3. Now, the arrangement emitted of the ion generating units will be described with reference to relevant figures.

Figure 13:
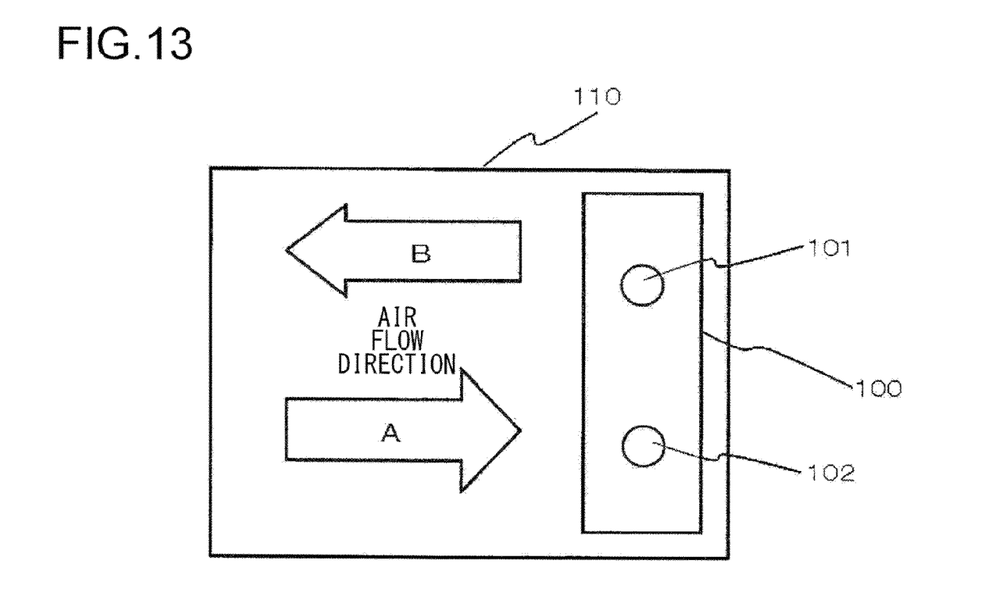
FIG. 13 is a diagram showing an example where an ion generating device is arranged along a direction crossing a direction in which a flow of air is sent from a blower.

As shown in FIG. 13, an ion generating device 100 is mounted inside an ion generator 110 such that a direction of a straight line connecting centers of the positive and negative ion generating units 101 and 102 crosses (substantially orthogonally) direction A or direction B in which air is sent from a blower (unillustrated) that is arranged inside the ion generator 110.

However, with such a mounting method, width of an external housing of the main body of the ion generator 110 in the direction of a straight line connecting the ion generating units at least needs to be greater than width of the ion generating device 100 in the longitudinal direction. This will restrict width of a space where the ion generator can be placed. For example, the ion generator 110 can be placed without problems in a space (gap) of a width greater than the width of the ion generator 110, but it cannot be placed in a space of a width smaller than the length between the ion generating units. This puts a restriction on where the ion generator 110 can be placed, and to deal with this inconvenience, it is desirable to provide a thin ion generator that can be placed even in a narrow space.

Figure 14:
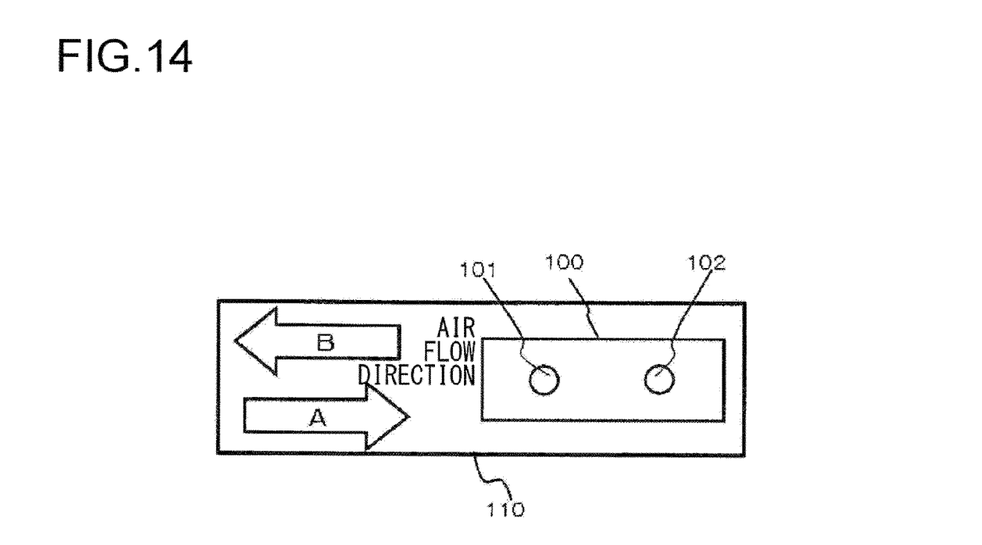
FIG. 14 is a diagram showing an example where an ion generating device is arranged along a direction in which a flow of air is sent from a blower.

If, in order to cope with this problem, the ion generating device is arranged such that a straight line connecting the positive ion generating unit 101 and the negative ion generating unit 102 extends parallel to the flow of air sent from the blower as shown in FIG. 14, the length of the ion generator 110 in the air flow direction is increased, and the width in the direction perpendicular to the length is reduced. As shown in FIG. 14, if the ion generating device 100 is placed such that a straight line connecting the centers of the positive and negative ion generating units 101 and 102 extends along the air flow direction, the width of the ion generator 110 becomes about the width of the ion generating device 100 in the short-side direction.

Unfortunately, however, with such an arrangement, positive ions generated at a windward side is affected by negative ions generated at a leeward side, and the positive ions reduces. That is, the positive ions generated at the windward side combine with the negative ions generated at the leeward side to be neutralized, and a large amount of generated ions are lost. This makes it difficult to have large amounts of positive and negative ions emitted out of the ion generator 110 in a balanced manner, allowing emission of only very small amounts of positive and negative ions.

The present invention primarily aims to provide an ion generator capable of being placed in a narrow space.

An object of the present invention is to provide an ion generator capable of effectively emitting generated positive and negative ions.

Another object of the present invention is to provide a thin ion generator capable of effectively emitting generated positive and negative ions. Specifically, the present invention aims to provide an ion generator capable of reducing the amount of disappearance of ions as much as possible to emit a lot of positive and negative ions.

Still another object of the present invention is to improve balance between the positive and negative ions to be emitted to outside of the ion generator.

Solution to Problem

To achieve the above objects, according to the present invention, an ion generator includes an ion generating device having a positive ion generating unit and a negative ion generating unit, disposed such that the positive ion generating unit and the negative ion generating unit are arranged apart from each other in the air flow direction, one at a windward side and the other at a leeward side.

Furthermore, for the purpose of preventing positive and negative ions from combining with each other, a partition member is provided to separate an air flow path into two separate air passages, namely, an air passage for positive ions and an air passage for negative ions.

Moreover, in the ion generator of the present invention, the separate air passages separated by the partition member are constructed such that a flow rate of an air flow passing by the ion generating unit arranged at the windward side is different from a flow rate of an air flow that passes by the ion generating unit arranged at the leeward side.

The partition member is shaped such that the flow rate of the air flow passing by the ion generating unit arranged at the windward side is larger than that of the air flow passing by the ion generating unit arranged at the leeward side.

The flow rate of the air flow passing by the ion generating unit arranged at the windward side is 2.5 times larger than that of the air flow passing by the ion generating unit arranged at the leeward side.

Besides, in a case where positive and negative ions are emitted, for the purpose of preventing reduction of negative ions, which are more prone to be affected by environment than positive ions, the negative ion generating unit is arranged closer to an outlet port than the positive ion generating unit. That is, the negative ion generating unit is arranged at the leeward side.

Advantageous Effects of Invention

In cases where width of a space for placing an ion generator or an ion generating device is limited and thus positive and negative ion generating units of an ion generating device have to be aligned along a direction parallel to the direction of an air flow sent from a blower, it is possible to achieve well-balanced emission of positive and negative ions. This helps preferably achieve killing of floating molds and germs, inactivation of viruses and allergens, and removal of electricity from a space and an object.

DESCRIPTION OF EMBODIMENTS

Hereinafter, descriptions will be given of the construction of an ion generator according to the present invention with reference to the accompanying drawings.

(Basic Construction of Ion Generator)

Figure 1:
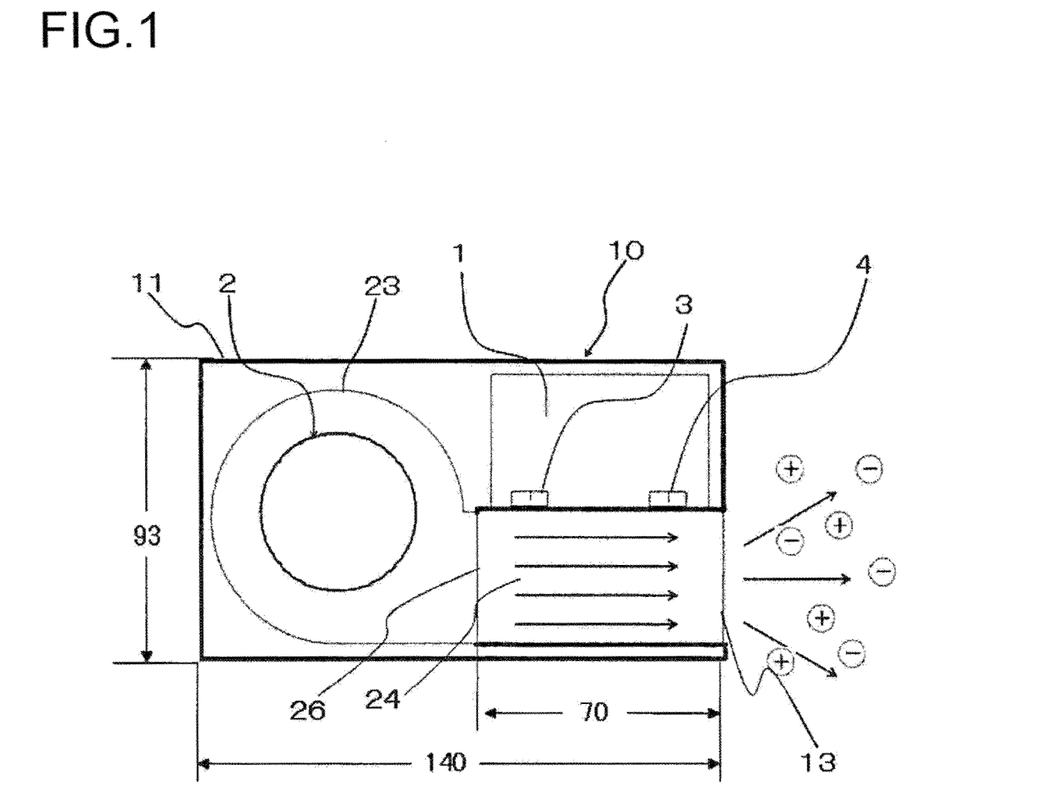
FIG. 1 is a schematic construction diagram showing an inner construction of an ion generator according to a basic construction of the present invention as seen laterally, where an ion generating device is disposed parallel to a flow of air sent from a blower.
Figure 2:
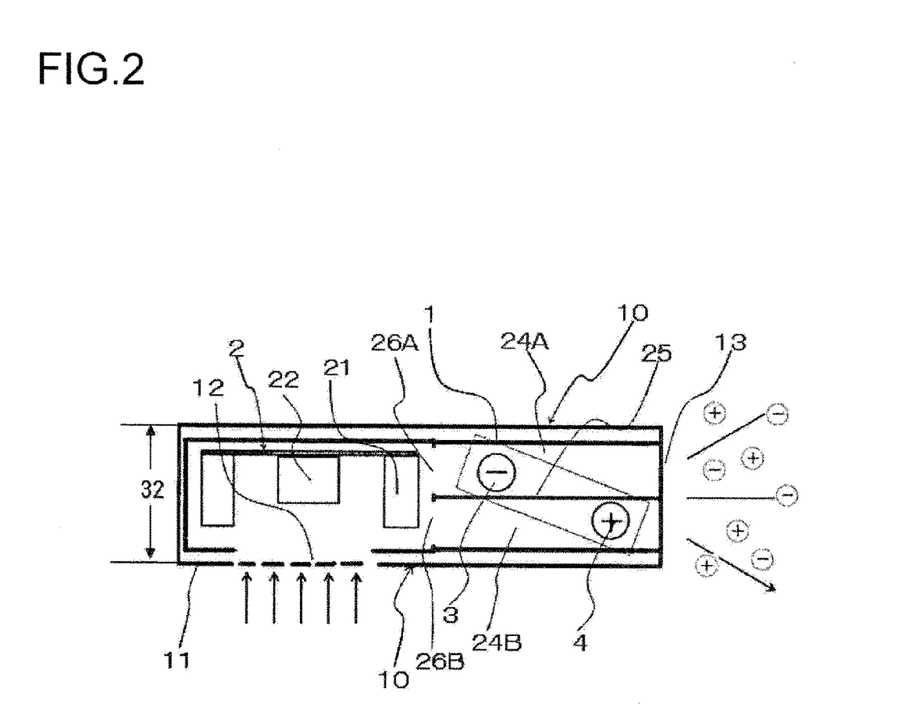
FIG. 2 is a schematic construction diagram showing the inner construction of the ion generator according to the basic construction of the present invention as seen from above, where the ion generating device is disposed parallel to a flow of air sent from the blower.
Figure 3:
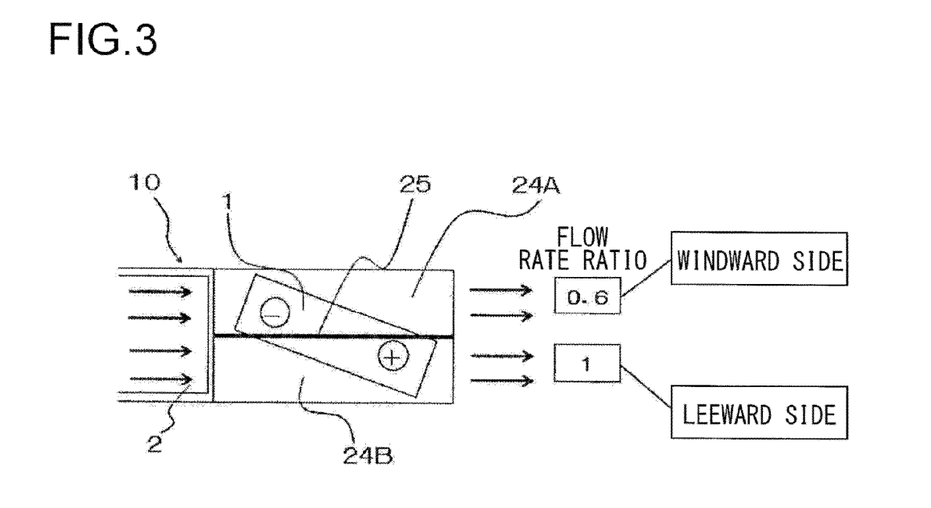
FIG. 3 is a diagram showing, together with the inner construction of the ion generator according to the basic construction, a flow rate ratio between air passages into which an air passage is separated.

FIGS. 1 through 3 are figures for illustrating the construction of an ion generator according to a basic construction of the present invention. FIG. 1 is a schematic diagram showing an inner construction of an ion generator as seen laterally, FIG. 2 is a diagram showing, as seen from above, an arrangement construction in an air flow direction in which air flows, and FIG. 3 is a diagram for illustrating the difference in flow rate.

First, with reference to FIG. 1, an ion generator 10 is provided with an ion generating device 1 that generates positive ions and negative ions separately from each other in a housing 11 serving as an external housing of the ion generator 10. Beside the ion generating device 1, that is, on the left side in FIG. 1, there is provided a blower 2 for discharging the generated ions to outside of the ion generator 10. The blower 2 has, for example, a sirocco fan 21 as shown in FIG. 2, and is also provided with a motor 22 for driving the sirocco fan 21. The fan constituting the blower 2 is not limited to a sirocco fan, but a fan of any construction may be adopted as long as it is built for blowing air.

The housing 11 has a shape of a rectangular parallelepiped, for example, and has an inlet port 12 which faces the sirocco fan 21 constituting the blower 2 and through which outside air is sucked into the housing 11. In relation to the inlet port 12, there is formed a discharge port 13 on a surface side in a direction perpendicular to the direction in which the inlet port 12 is opened; air sucked in from outside and turned toward the ion generating device 1 by the operation of the sirocco fan 21 is discharged to the outside of the ion generator 10 through the discharge port 13. An air passage 24 is provided downstream from the blower 2 and connected to the blower 2; a positive ion generating unit 4 and a negative ion generating unit 3 of the ion generating device 1 are located along the air passage 24. The air passage 24 is part of an air flow path connecting the inlet port 12 and the discharge port 13, and the blower 2 is disposed upstream in the air flow path.

The blower 2 has an air-flow guide 23 so formed as to surround the outer periphery of the sirocco fan 21 with a predetermined width of gap therebetween. The air-flow guide 23 is connected with an inflow port 26 of the air passage 24, such that sucked-in air can be effectively sent through the discharge port 13 via the ion generating device 1.

The ion generating device 1 is provided with the negative ion generating unit 3 and the positive ion generating unit 4 which separately generate positive ions and negative ions, respectively. The ion generating device 1 is arranged such that the negative ion generating unit 3 and the positive ion generating unit 4 are located along the air passage 24 with their ion emitting ports facing the air passage 24.

The negative ion generating unit 3 and the positive ion generating unit 4 of the ion generating device 1 are arranged, for example, along a direction that is inclined with respect to the air passage 24 as shown in FIG. 2. That is, the positive ion generating unit 4 and the negative ion generating unit 3 are arranged such that a straight line connecting centers of the negative and positive ion generating units 3 and 4 is inclined with respect to an air flow direction in which air flows through the air passage 24. In FIG. 2, along the air passage 24, the negative ion generating unit 3 is arranged at a windward side while the positive ion generating unit 4 is arranged at the leeward side.

The air passage 24 is provided with a partition member 25 for separating the air passage 24 by dividing a portion of the air passage 24 from the inflow port 26 through the discharge port 13 into two parts. The negative ion generating unit 3 is located along a first air passage 24A, which is one of the two parts of the air passage 24 divided by the partition member 25, while the positive ion generating unit 4 is located along a second air passage 24B, which is the other of the two parts of the air passage 24 divided by the partition member 25. With this arrangement, negative ions generated by the negative ion generating unit 3 located at the windward side are conveyed by a flow of air sent from the blower 2 to pass through the first air passage 24A and emitted through the discharge port 13, while being prevented from being neutralized by combining with positive ions generated by the positive ion generating unit 4 at the leeward side. In contrast, positive ions generated by the positive ion generating portion 4 located at the leeward side are emitted through the discharge port 13 as they are, without being combined with the negative ions in the air passage 24.

Thus, the negative and positive ions generated separate from each other by the ion generating device 1 are effectively emitted through the discharge port 13. With this arrangement, where the negative ion generating unit 3 and the positive ion generating unit 4 of the ion generating device 1 are arranged apart from each other along the air flow direction in which air flows through the air passage 24, the size (width) in a direction perpendicular to the air flow direction is not increased, and thus it is possible to provide an ion generator 10 having as small a width as possible.

Furthermore, according to the ion generator 10, where positive and negative ions are emitted through the discharge port 13 while being prevented by the partition member 25 from combining with each other inside the air passage 24, it is possible to effectively deliver the generated positive and negative ions to the outside of the ion generator 10.

Thus, the ion generator 10 is able to be set in a narrow limited space, restriction on the setting place thereof being reduced, to eliminate germs, kill germs, and remove odors and the like by means of the generated ions.

Next, verification was conducted, by using an ion generator according to the above-described basic construction, to improve the efficiency of the present invention in generating positive and negative ions. The ion generators 10 shown in FIG. 1 and other figures were each provided with a partition member 25 to separate the positive ion generating unit 4 from the negative ion generating unit 3, to thereby obtain an ion generator capable of reducing, as much as possible, amount of ions lost by, for example, positive and negative ions combining with each other, and capable of efficiently emitting positive and negative ions to achieve a good ion balance.

(Verification of Basic Construction)

The ion generator 10 having the basic construction is, as described above, provided with the partition member 25 disposed between the positive ion generating unit 4 and the negative ion generating unit 3 to separate them from each other, for the purpose of preventing ions generated at the leeward side from affecting those generated at the windward side. The separation is made in the ion generating device 1 by dividing the air passage 24, through which air flows, into two equal portions (that are equal in sectional area as well) with the partition member 25. Besides, the ion generating device 1 is placed such that the positive ion generating unit 4 and the negative ion generating unit 3 are arranged along a direction parallel to the direction in which a flow of air is sent from the blower 2. Also, the positive ion generating unit 4 and the negative ion generating unit 3 are placed such that a straight line connecting their centers is inclined such that the negative and positive ion generating units 3 and 4 are respectively corresponding to the air passages 24A and 24B which are separated by the partition member 25.

The size of the external housing of the ion generator 10 in which the ion generating device 1 is mounted, that is, the dimension of the ion generator 10, will be described below.

Let the direction of the flow of air blown out from the blower 2 be a front-rear direction, the discharge-port-13 side be a front side, and the side opposite to the front side be a rear side. The length (depth) in the front-rear direction was set to be 140 mm as shown in FIG. 1; in FIG. 1, let the ion-generating-device-1 side be an upper side, and the air-passage-24 side be a lower side, the height between the upper and lower sides was set to be 93 mm; and the width in the right-left direction as seen from the discharge-port-13 side of the ion generating device 10 in FIG. 2 was set to be 32 mm.

As the fan of the blower 2, the sirocco fan 21 was provided, and the maximum flow rate was set to be 0.39 m$^3$/min. Here, the negative and positive ion generating units 3 and 4 are arranged at the windward side and leeward side, respectively, with respect to the direction in which the flow of air is sent from the blower 2. The partition member 25 was provided between the two ion generating units 3 and 4, such that the air passage 24 where the flow of air passes by the two ion generating units 3 and 4 were separated into the first air passage 24A and the second air passage 24B, that is, the air passage 24 was divided into two equal portions.

In this case, despite the fact that the two air passages 24A and 24B had the same sectional area, the ratio between the flow rate in the first air passage 24A and the flow rate in the second air passage 24B was actually 0.6:1, as measured at the discharge port 13. That is, the flow rate in the air passage 24B was larger than the flow rate in the air passage 24A, the former being approximately double the latter. This was caused partly by the characteristic of the sirocco fan 21, and also caused by the fact that the flow of air sent from the sirocco fan 21 was not stable because the distance between a discharge port (at an air-inlet side of the air passage 24) of the sirocco fan 21 and the discharge port 13 of the ion generator 10 was as short as about 70 mm as shown in FIG. 1.

Figure 4:
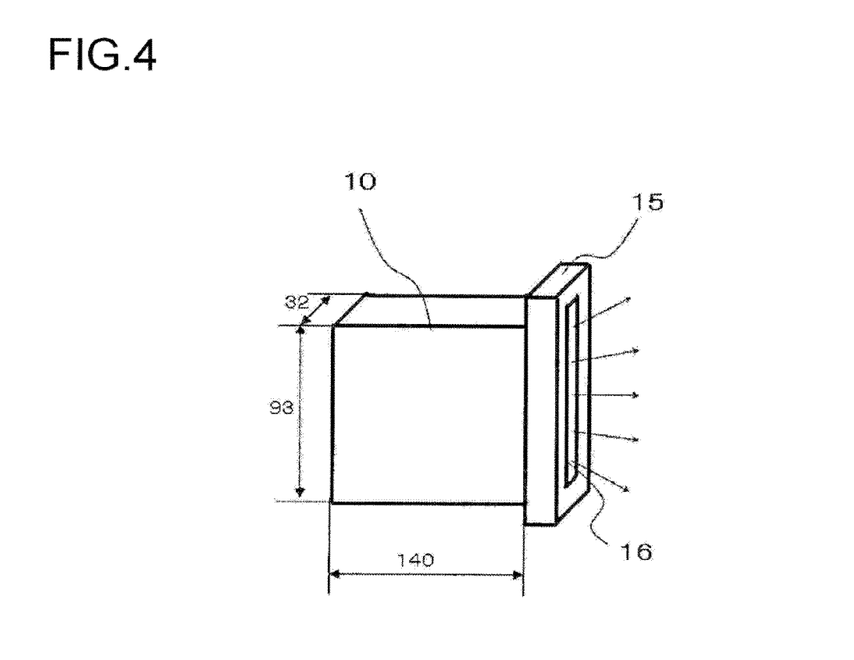
FIG. 4 is a perspective view showing a state where an ion scattering device is attached to a discharge port of the ion generator.
Figure 5:
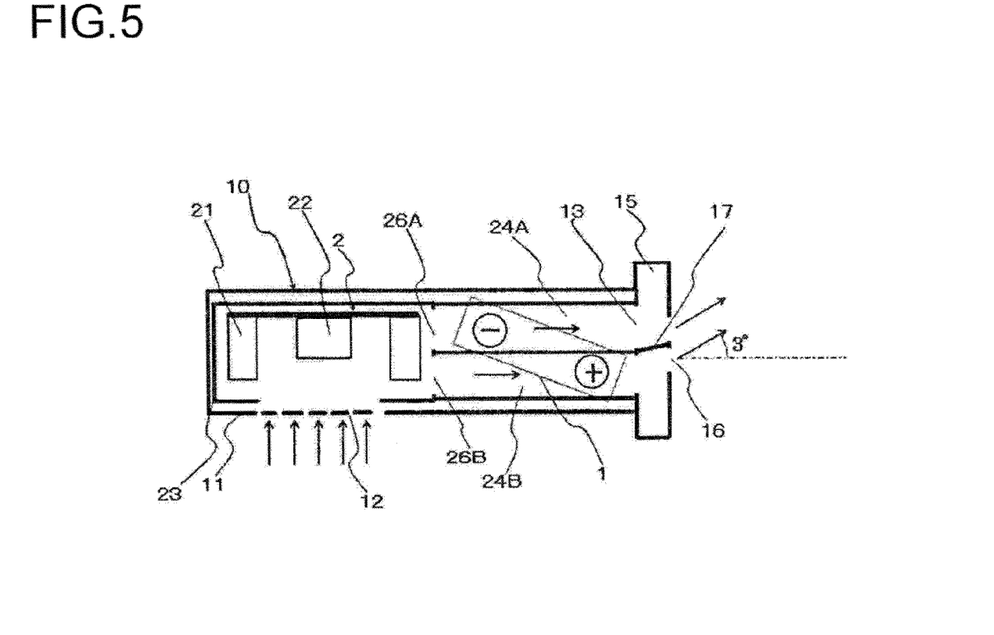
FIG. 5 is a schematic construction diagram showing an example of the construction of an ion generating device to which the ion scattering device is attached.

To the ion generator 10, an ion scattering device 15 as shown in FIG. 4 was attached at the discharge port 13. A discharge port 16 of the ion scattering device 15 was formed over the discharge port 13 of the ion generator 10, even over a part of the ion generator 10 where the discharge port 13 corresponding to the ion generating device 1 did not exist. For the purpose of allowing air to be blown even through a portion facing the ion generating device 1, the discharge port 16 of the ion scattering device 15 was formed to be narrower than the width of the discharge port 13 and also to extend to the ion generating device 1 side. Moreover, a deflecting plate (deflecting member) 17 was provided extending from an edge of the partition member 25 in an inclined manner such that the airflow direction was inclined by about 3° inward from a frontward air blowing direction of the ion scattering device 15 as shown in FIG. 5.

Figure 6:
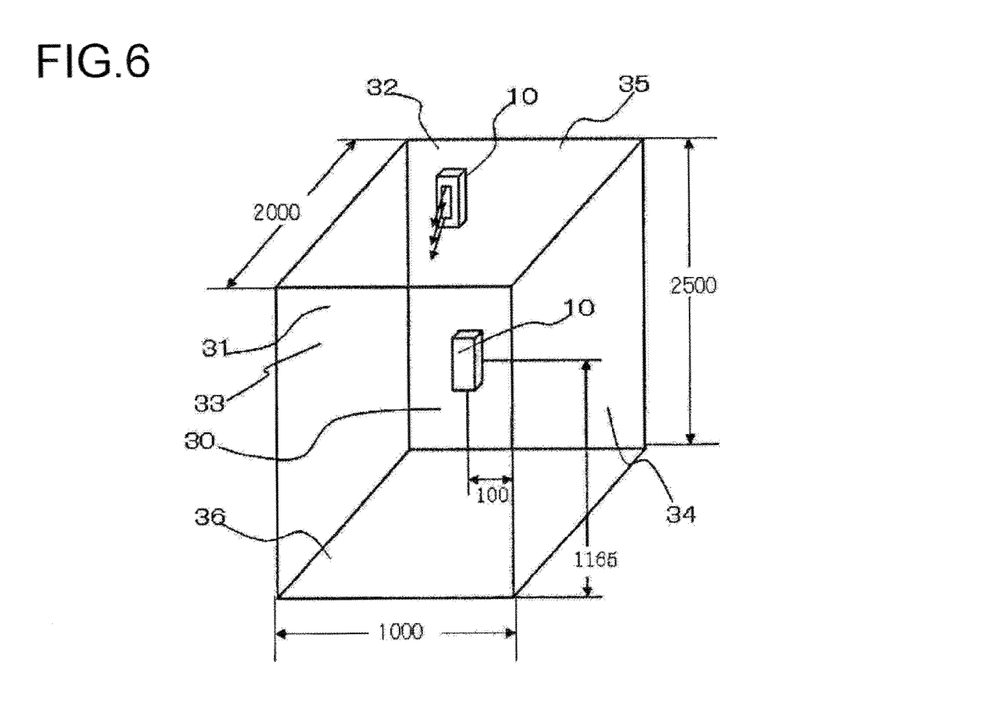
FIG. 6 is a diagram showing an outline of a space where concentrations of ions generated by ion generators are measured, the diagram also showing arrangement of the ion generators.

A space for measuring ions was prepared to verify the state of ion balance generated by the ion generator 10 to which the above-described ion scattering device 15 was attached. The space was one that was enclosed by walls as shown in FIG. 6. In the space 30 as shown in FIG. 6, the above-described ion generator 10 was arranged.

The space 30 was enclosed by front and rear walls 31 and 32 to which two ion generators 10 were attached, right and left side walls 33 and 34 on the right and left of the ion generators 10, and a top wall 35 and a bottom wall (bottom surface) 36 facing each other in the up-down direction.

One of two ion generators 10 was attached to the front wall 31 such that the discharge port 13 thereof faced the rear wall 32 while the other was attached to the rear wall 32 such that the discharge port 13 thereof faced the front wall 31. As for the size of the space 30, that is, the volume of the space 30, as shown in FIG. 6, the distance (depth) between the front and rear walls to which the ion generators 10 were attached was 2000 mm (2 m), the distance between the top and bottom walls 35 and 36 in the up-down direction was 2500 mm (2.5 m), and the width between side surfaces of the side walls 33 and 34 serving as side surfaces of the space was 1000 mm (1 m).

Figure 7:
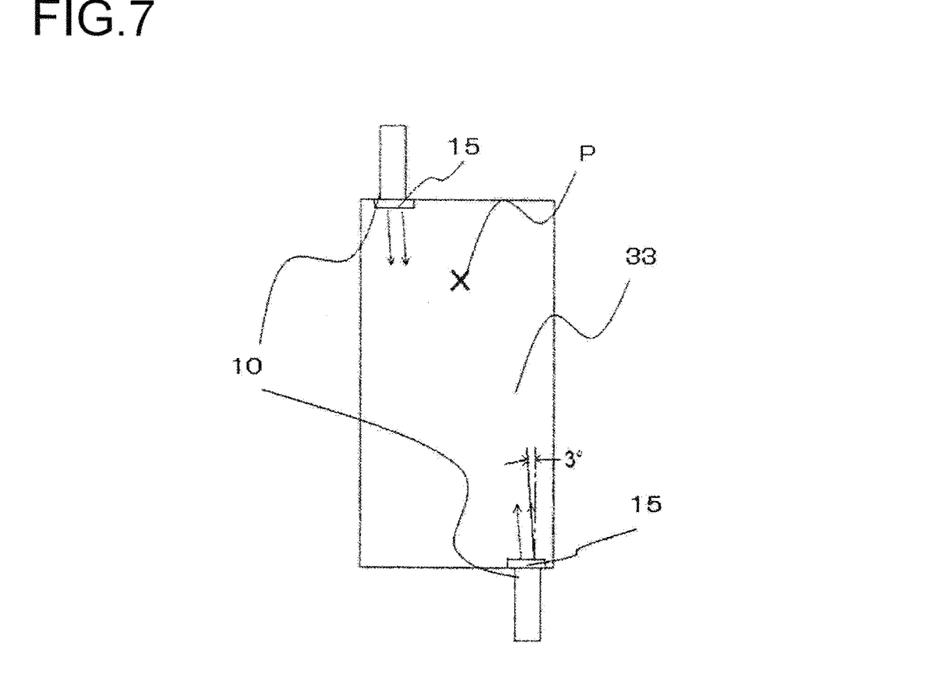
FIG. 7 is a diagram showing the arrangement of the ion generators as seen from above the space where the ion concentration measurement shown in FIG. 6 is conducted.

The ion generators 10 were fitted to the front and rear surfaces of the space 30 such that the centers of their discharge ports 16 were each 100 mm away from either the right wall or the left wall, and 1165 mm above the bottom surface in FIG. 6. Besides, as shown in FIG. 7, each of the ion generators 10 was provided with the above-described ion scattering device 15 constructed to allow air to flow into the space 30 at an angle of about 3° inward with respect to the surfaces of the side walls 33 and 34.

In order to verify the amount of ions emitted when the ion generators 10 arranged as described above were driven, ion concentration measurement was conducted by using an ion counter. The ion counter was placed such that the ion counter setting position, that is, a measuring point P was 1200 mm above the bottom plate (bottom wall) 36, 500 mm away from either of the side walls 33 and 34, and 500 mm away from the rear wall to which one of the ion generators 10 was attached.

The result of the ion concentration measurement conducted under the condition shown in FIGS. 6 and 7 will be shown in Table 1 below.

TABLE 1

| Ion Concentration (ions/cm$^3$) | | Ion Balance |
|---|---|---|
| Positive Ion | Negative Ion | (+/−) |
| 32,600 | 11,000 | 2.96 |

According to the results shown above in Table 1, the concentration of positive ions was higher than that of negative ions. This occurred because the positive ions generated at the leeward side where the flow rate was large affected the negative ions generated at the windward side. Specifically, the positive ion concentration was 32,600 ions/cm3 while the negative ion concentration was 11,000 ions/cm3, the concentration of the positive ions at the leeward side was about three times as high as that of the negative ions. Thus, the ion balance was not much improved by simply separating the air passage 24 by means of the partition member 25 into two equal air passages corresponding to the two ion generating units 3 and 4.

Thus, in the ion generator 10 according to the basic construction, the ion balance was not improved by providing the partition member 25 for separating from each other the positive and negative ions generated by the positive and negative ion generating units 4 and 3, to prevent the positive and negative ions from interfering with each other. However, the concentration of negative ions was also comparatively high, and thus, it can be said that the provision of the partition member 25 to separate the air passage into air passages respectively corresponding to the two ion generating units was effective to some extent.

Now, descriptions will be given, one by one, of constructions according to preferred embodiments of the present invention based on, and capable of improving the ion balance more than, the construction of the ion generator 10 according to the basic construction.

FIRST EMBODIMENT

Figure 8:
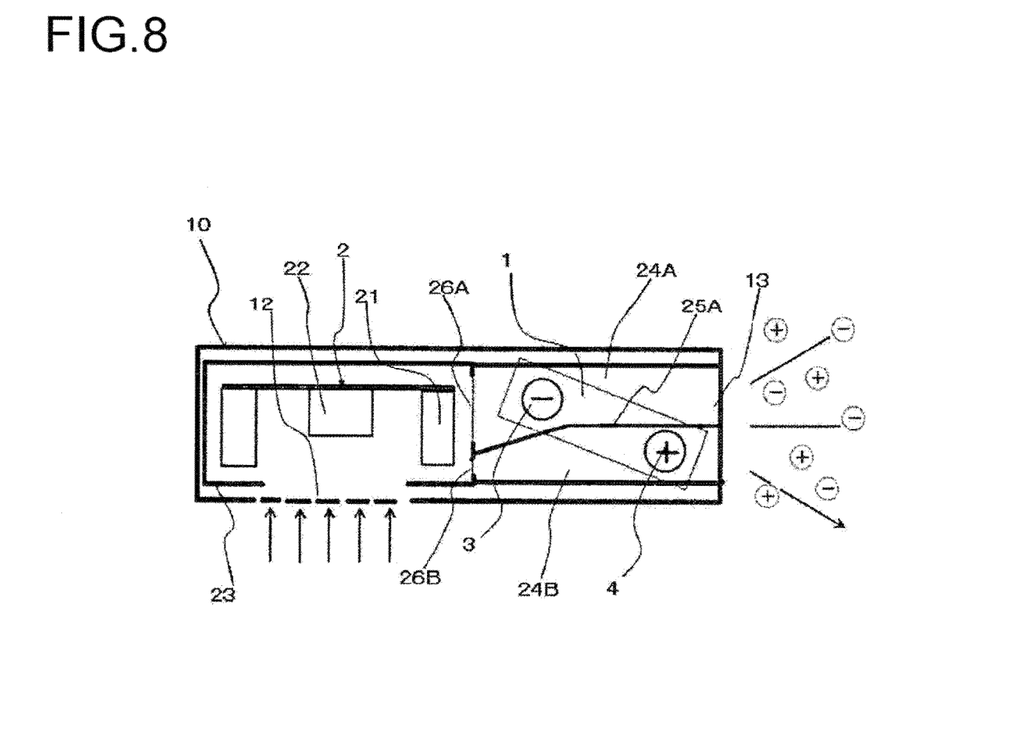
FIG. 8 is a schematic construction diagram as seen from above for illustrating the construction of an ion generator according to a first embodiment of the present invention.

FIG. 8 is a diagram showing an ion generator 10 according to a first embodiment. The figure shows an internal construction of the ion generator 10, and is particularly related to the ion generator 10 shown in FIG. 2 which has been referred to in the description of the basic construction. For the convenience of description, ion generators of all the embodiments will be given the same reference sign 10. Of the ion generators 10 described below, parts and portions that are different from their counterparts in the basic construction will be given different signs, and only details thereof will be given. That is, the same reference signs are used to indicate the same or similar elements as in the basic construction.

The ion generator 10 according to the first embodiment is different from the ion generator 10 according to the basic construction described above in the partition member 25. In particular, the partition member in the first embodiment is denoted by a reference sign 25A as shown in FIG. 8.

The partition member 25A of the first embodiment is dog-leg shaped such that, of the partition member 25A provided as a partition for dividing an air passage 24 into two parts of first and second air passages 24A and 24B, a portion extending from the vicinity of the center to the windward side is bent toward an inlet port 12. That is, the sectional area of an inflow port 26A of the first air passage 24A is made larger than that of an inflow port 26B of the second air passage 24B. This is adopted to increase the flow rate ratio of the first air passage 24A along which a negative ion generating unit 3 is placed at the windward side by making the sectional area of the inflow port 26A of the first air passage 24A larger than that of the second air passage 24B, to thereby achieve an improved balance between positive and negative ions. That is, the partition member 25A divides the air passage 24 into the first and second air passages 24A and 24B such that the flow rate in the first air passage 24A is different from the flow rate in the second air passage 24B; specifically, the flow rate in the first air passage 24A is larger than the flow rate in the second air passage 24B.

Figure 9:
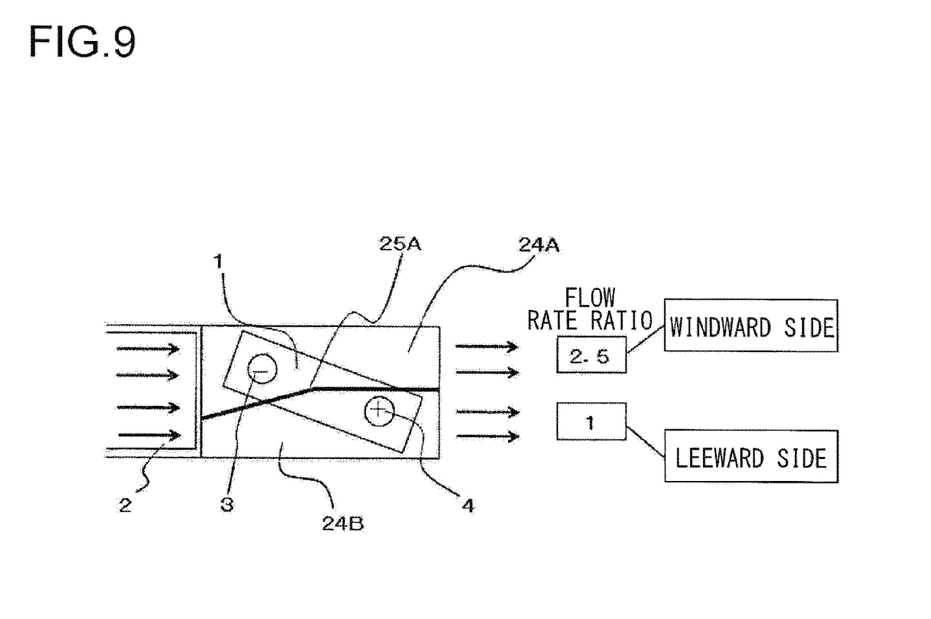
FIG. 9 is a diagram for illustrating difference in flow rate between two air passages according to the first embodiment of the present invention.

Here, the sectional area ratio at the inflow ports 26A and 26B of the first and second air passages 24A and 24B, respectively, was 3:1. With this construction, the flow rate ratio between the first and second air passages 24A and 24B at a discharge port 13 was, as shown in FIG. 9, 2.5:1.

To the ion generator 10 using the partition member 25A, an ion scattering device 15 was attached facing the discharge port 13 like in the basic construction, and in the same manner as in the verification of the basic construction, ion concentration measurement was conducted in the space 30 shown in FIGS. 6 and 7. The result of the measurement was as shown in Table 2.

TABLE 2

| Ion Concentration (ions/cm³) | | Ion Balance |
| --- | --- | --- |
| Positive Ion | Negative Ion | (+/−) |
| 37,500 | 25,100 | 1.49 |

With the ion generator 10 of the first embodiment, positive and negative ion concentrations were 37,500 ions/cm³ and 25,100 ions/cm³, respectively. In terms of the ion balance between the positive and negative ions, the positive ion concentration was about 1.5 times as high as the negative ion concentration. Thus, despite the 2.5 times larger flow rate, the amount of ions at the windward side was smaller than that at the leeward side. However, the ion balance was improved and better.

As described above, the ion generator 10, where the partition member 25A is used to divide the air passage 24 into the first and second air passages 24A and 24B corresponding to the negative and positive ion generating units 3 and 4, is constructed such that the flow rate in the second air passage 24B located on the inlet port 12 side is smaller than the flow rate in the first air passage 24A. This construction was adopted for the purpose of improving the balance between positive and negative ions, and helped greatly improve the ion balance. This made it possible to enhance the advantages obtained thanks to positive and negative ions.

In the first embodiment, the partition member 25 has a shape for dividing the air passage 24 such that the flow rate in the first air passage 24A provided for the negative ion generating unit 3 disposed at the windward side is larger than the flow rate in the second air passage 24B provided for the positive ion generating unit 4 disposed at the leeward side. That is, the partition member 25 is formed in a shape that changes the sectional area of the air passage 24 at the inflow port 26.

SECOND EMBODIMENT

Figure 10:
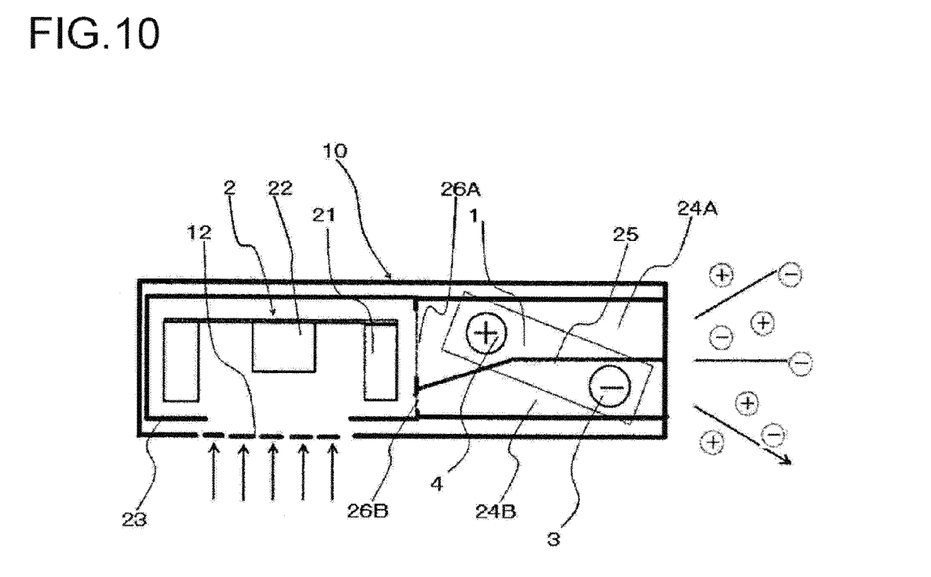
FIG. 10 is a schematic construction diagram as seen from above for illustrating the construction of an ion generator according to a second embodiment of the present invention.

FIG. 10 is a diagram showing construction of an ion generator 10 according to a second embodiment of the present invention. The ion generators 10 of the first and second embodiments are different from each other in that the arrangement of negative and positive ion generating units 3 and 4 in an ion generating device 1 of the second embodiment is opposite to that of the negative and positive ion generating units 3 and 4 in the ion generating device 1 of the first embodiment.

With respect to the ion generator 10 of the second embodiment as well, measurement of ion concentration was conducted inside the space shown in FIGS. 6 and 7, in the same manner as was conducted with respect to the ion generator 10 of the first embodiment. In the ion generator 10 of the second embodiment as well, like in the ion generator 10 of the first embodiment, the flow rate ratio between first and second air passages 24A and 24B was equal to the flow rate ratio indicated in FIG. 9.

That is, the sectional area ratio at inflow ports 26A and 26B of the first and second air passages 24A and 24B, respectively, was 3:1. With this construction, the flow rate ratio between the first and second air passages 24A and 24B at a discharge port 13 of the ion generating device 10 was 2.5:1.

The ion scattering device 15 was attached to the ion generator 10 according to the second embodiment, and ion concentration was measured inside the space 30 shown in FIG. 6 and FIG. 7. The result of the measurement was as shown in Table 3.

TABLE 3

| Ion Concentration (ions/cm³) | | Ion Balance |
| --- | --- | --- |
| Positive Ion | Negative Ion | (+/−) |
| 30,700 | 32,600 | 0.94 |

As shown in Table 3, positive and negative ion concentrations were 30,700 ions/cm³ and 32,600 ions/cm³, respectively, and thus the ion balance in this case was the best. In contrast to the result obtained with the ion generator 10 of the first embodiment, the negative ion concentration was higher than the positive ion concentration, and in addition, in comparison with the result obtained with the ion generator 10 of the first embodiment, the reduction ratio of positive ions was about 18% while the increase ratio of negative ions was about 30%, that is, the positive ion concentration did not decrease as much as the negative ion concentration increased. This occurred because positive ions are less likely to disappear than negative ions, as can be understood from the fact that there exist more positive ions than negative ions in nature.

Thus, by using the partition member 25A and disposing the positive ion generating unit 4 at the windward side and the negative ion generating unit 3 at the leeward side, it is possible to create a space having a good ion balance even by using the ion generator 10 where the ion generating device 1 is used by being placed substantially parallel to an air flow direction in which air flows.

As described above, the second embodiment as well is provided with the ion scattering device 15 that creates an air curtain by using air blown from the ion generating device 10. In addition to the constructions where the ion generating device 10 is provided with the ion scattering device 15 having the air-curtain creating function as in the second embodiment, and in the first embodiment as well, the present invention is applicable to an air purifier that has an ion generating device 1 and sends purified air into a room and to a method of purifying air by using such an air purifier. This is true of the following embodiments as well.

THIRD EMBODIMENT

Figure 11:
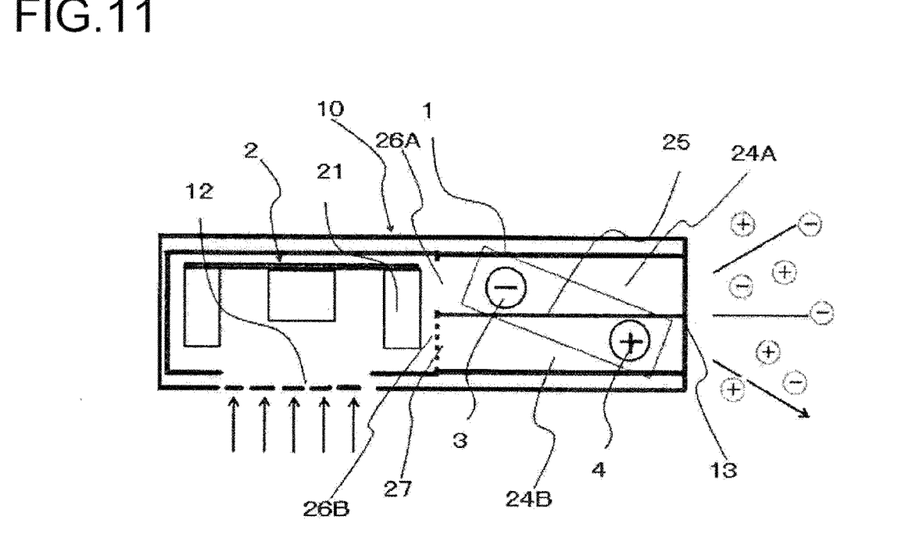
FIG. 11 is a schematic construction diagram as seen from above for illustrating the construction of an ion generator according to a third embodiment of the present invention.

FIG. 11 is a diagram showing construction of an ion generator 10 according to a third embodiment of the present invention. The ion generator 10 of the third embodiment is different from that of the first embodiment in that an air passage 24 is separated by a partition member 25 that is similar to the partition member 25 used in the basic construction. Besides, the ion generator 10 of the third embodiment is different from that of the basic construction in that, for the purpose of controlling the flow rates through first and second air passages 24A and 24B such that the ratio between the two flow rates is 2.5:1 like in the above descriptions, a resistant element 27 is provided at an inflow port 26B for restricting the flow rate in the second air passage 24B. By providing the resistant element 27 in this way, it is possible to obtain the same effect as is obtained by reducing the sectional area of the inflow port 26B side by using the partition member 25A.

Thus, by providing the resistant element 27, the flow rate in the second air passage 24B was restricted, and thereby, the ratio between the flow rates in the first and second air passages 24A and 24B was adjusted to be 2.5:1 as described above.

With respect to the ion generator 10 of the third embodiment as well, measurement of ion concentration was conducted inside the space shown in FIGS. 6 and 7, in the same manner as was conducted with respect to the ion generator 10 of the first embodiment. In the ion generator 10 of the third embodiment as well, like in the ion generator 10 of the first embodiment, the flow rate ratio between first and second air passages 24A and 24B was set to be the same as in the above descriptions.

An ion scattering device 15 was attached to the ion generator 10 according to the third embodiment, and ion concentration was measured inside the space 30 shown in FIG. 6 and FIG. 7. The result of the measurement was as shown in Table 4.

TABLE 4

| Ion Concentration (ions/cm$^3$) | | Ion Balance |
|---|---|---|
| Positive Ion | Negative Ion | (+/−) |
| 37,500 | 25,100 | 1.49 |

Thus, according to the third embodiment, the construction of the ion generator 10 is similar to that according to the basic construction of the present invention, and the ion generating device 1 is similar to that of the first embodiment except that the resistant element 27 is provided to adjust the flow rate ratio between the first and second air passages 24A and 24B to be 2.5:1. With the third embodiment as well, there was obtained the same result as was obtained with the first embodiment.

Besides, according to the ion generator 10 of the third embodiment, the provision of the resistant element 27 makes it possible to adjust the flow rate ratio between the first and second air passages 24A and 24B. In particular, it is possible to form the partition member 25 in a linear shape, which is advantageous in terms of fabrication.

As the resistant element 27, a mesh, a lattice, a perforated plate, etc. may be used.

FOURTH EMBODIMENT

Figure 12:
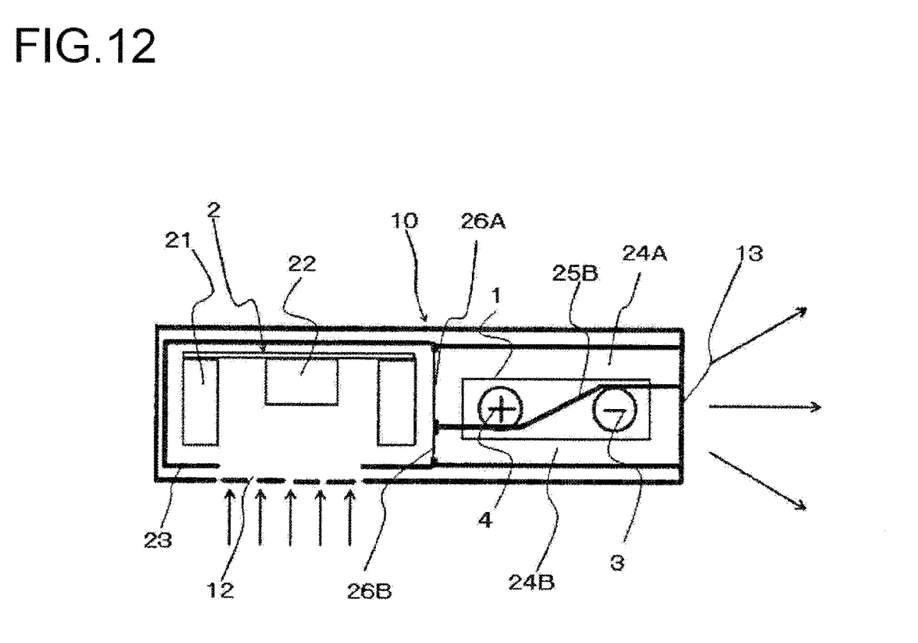
FIG. 12 is a schematic construction diagram as seen from above for illustrating the construction of an ion generator according to a fourth embodiment of the present invention.

FIG. 12 is a diagram showing the construction of an ion generator 10 according to a fourth embodiment of the present invention. As shown in FIG. 12, the ion generator 10 of the fourth embodiment is arranged such that a straight line connecting centers of negative and positive ion generating units 3 and 4 extends along an air flow direction in which air flows through an air passage 24. Here, a partition member 25B for separating the air passage 24 into first and second air passages 24A and 24B to which inflow ports 26A and 26B correspond, respectively, is formed such that the sectional area ratio between the inflow ports 26A and 26B is 3:1, that is, the sectional area of the inlet port 26A is three times as large as that of the inlet port 26B.

The partition member 25B is also formed such that the sectional area ratio between the first and second air passages 24A and 24B at a discharge port 13 is opposite to that at the inflow ports 26A and 26B. And the partition member 25B has an inclined center portion, that is, obliquely extends in a center portion of the air passage 24, and thus separates the air passage 24. The inclined portion may be a curved portion instead.

According to the partition member 25B of the ion generator 10 according to the fourth embodiment as described above, even if the negative and positive ion generating units 3 and 4 of the ion generating device 1 are linearly aligned along the air flow direction, it is possible to achieve the same level of flow rate ratio between the first and second air passages 24A and 24B as achieved in the first to third embodiment. As a result, in the ion generating device 1, by arranging the positive ion generating unit 4 at the windward side along the first air passage 24A and the negative ion generating unit 3 at the leeward side along the second air passage 24B, it is possible to expect about the same operation/working-effect as is obtained in the second embodiment.

Furthermore, in the ion generating device 1, by arranging the negative ion generating unit 3 at the windward side along the first air passage 24A and the positive ion generating unit 4 at the leeward side along the second air passage 24B, it is possible to expect about the same operation/working-effect as is obtained in the first and third embodiments.

Moreover, according to the fourth embodiment, the positive ion generating portion 4 and the negative ion generating portion 3 of the ion generating device 1 can be linearly arranged in the air flow direction, there is no need of arranging the ion generating device 1 obliquely, for example, and this makes it possible to further reduce the size in the width direction.

Features common to the constructions of the ion generators 10 of all the embodiments discussed above are as follows. The positive ion generating portion 4 and the negative ion generating portion 3 of the ion generating device 1 are arranged along the air passage 24 to be separate from each other at the windward and leeward sides in the air flow direction in which air flows through the air passage 24. Here, the air passage through which air flows passing by the positive ion generating unit 4 and the negative ion generating unit 3 is separated by the partition member 25, and the positive and negative ion generating unit 4 and 3 are arranged corresponding to the separated air passages on a one-to-one basis.

The air passages separated by the partition member 25 do not have the same flow rate, but have different flow rates. In particular, in a case where one of the ion generating units of the ion generating device 1 is arranged on the windward side along one of the air passages, the flow rate in the one of the air passages is set to be larger than the flow rate in the other of the air passages along which the other ion generating unit is arranged on the leeward side. This setting is achieved, for example, by making the air-inflow-side sectional area of the one air passage on the inflow side, through which air flows into the one air passage, larger than the sectional area of the other air passage on the inflow side. As a specific example, such setting is achieved by forming the partition member 25 in a shape that adjusts the sectional areas. It is also possible to provide a resistant element or the like on the inflow side of an air passage to restrict the flow rate in the air passage.

Furthermore, according to the present invention, the flow rate in one air passage corresponding to one ion generating unit that is located on the windward side in the air flow direction is made larger than the flow rate in the other air passage corresponding to the other ion generating unit that is located on the leeward side to be opposite from the one ion generating unit, and thereby, it is possible to obtain an improved ion balance.

In addition, the difference in flow rate between the air passages is such that the larger flow rate is about 2.5 times larger than the smaller flow rate. This makes it possible to obtain a good ion balance.

Besides, the positive ion generating unit is arranged on the windward side along the air passage. This makes it possible to further improve the ion balance.

In each of the ion generators 10 of the various embodiments and the basic construction described above, the positive ion generating unit 4 and the negative ion generating unit 3 are oppositely arranged, with the first air passage 24A defined as an air passage corresponding to a windward-side ion generating unit, and the flow rate in the first air passage 24A is set to be larger, for example, about 2.5 times larger, than the flow rate in the second air passage 24B which has been described as an air passage corresponding to a leeward side ion generating unit. Thus, in a case where the positive ion generating unit 4 and the negative ion generating unit 3 are oppositely arranged, with the second air passage 24B defined as the air passage corresponding to the windward-side ion generating unit, the flow rate in the second air passage 24B needs to be set larger, for example, about 2.5 times larger, than the flow rate in the first air passage 24A. In short, the flow rate in an air passage along which an ion generating unit is arranged at the windward side thereof needs to be set as described above.

Also, in a case where, instead of the blower 2 provided with the sirocco fan 21, a blower provided with other type of fan is used and the partition member 25 is provided to separate the air passage, the flow rate in one air passage along which an ion generating unit of the ion generating device 1 is arranged at the windward side thereof needs to be set larger, for example, about 2.5 times larger, than the flow rate of another air passage by devising an appropriate shape into which the partition member 25 should be formed to separate the air passages. Alternatively, a resistant element 27 may be provided on one side of the inflow port 26 of the air passage 24.

In the above descriptions, importance has been placed on the ratio of flow rates of air flowing through the air passages; however, since the flow rate ratio between two air passages is equivalent to the flow speed ratio between them as long as their sectional areas are the same, it is clear that, even if the "flow rate" is replaced by the "flow speed" in the descriptions above, it will not change the meanings of the descriptions. Thus, it is possible to achieve the constructions according to the above embodiments based on the flow speed ratio.

As has been described above, according to the ion generator 10 of the present invention, it is possible to reduce the width (size) in the width direction, that is, in the right-left direction when the discharge port 13 is seen from the front, and also to efficiently emit generated ions to the outside. The ion balance at this time can be improved. This helps reduce restrictions on setting space for the ion generator 10, making it possible to place the ion generator 10 even in a narrow space.

For example, in a game parlor and the like, in an environment where a large number of game machines are arranged side by side, where there is only a limited space for setting ion generators 10, it is possible to place the ion generator 10 even in such a narrow space. For example, in a place where people sit in front of game machines and enjoy playing on the game machines, it is possible to place the ion generators 10 in narrow spaces between adjacent game machines. Usually, the play machines, for example, pinball machines, slot machines, and the like are arranged such that a large number of them are arranged next to each other even behind the people each sitting in front of a game machine.

If ion generators 10 are also set in spaces between adjacent game machines in rows behind and ahead of a row, the ion generators 10 placed in spaces between adjacent game machines in a row and rows behind and ahead of the row together form a space 30 as shown in FIG. 6. In this case, despite the fact that there is no top wall 35, it is possible to create in the separated area of space an atmosphere containing comparatively high concentrations of positive and negative ions with ions generated by the ion generators 10.

In this way, it is possible to reproduce a space where adjacent game machines are separated from each other by the ion generators 10. Thus, it is possible to create a space comfortable to a person enjoying playing games where it is possible to remove, kill, or inactivate cigarette smell coming from a person sitting next to the person, and germs, molds, viruses, and the like included in the air in the space around the person.

LIST OF REFERENCE SYMBOLS 1 ion generating device
2 blower
3 negative ion generating unit
4 positive ion generating unit
10 ion generator
11 housing
12 air inlet port
13 discharge port
21 sirocco fan
22 motor
24 air passage
24A first air passage
24B second air passage
25 partition member
25A partition member
25B partition member
26 inflow port
26A inflow port (separate inflow port)
26B inflow port (separate inflow port)

The invention claimed is:
1. An ion generator, comprising:
an inlet port through which air is sucked in;
a discharge port through which air is discharged;
a blower that sucks in air through the inlet port and discharges the air through the discharge port;
an air passage connecting an outlet port of the blower and the discharge port; and
an ion generating device separately provided with a positive ion generating unit that generates positive ions and a negative ion generating unit that generates negative ions and disposed such that the positive ion generating unit and the negative ion generating unit face the air passage and the positive ions and the negative ions are discharged through the discharge port, wherein
a partition member is provided to separate the air passage into separate air passages;
one of the positive ion generating unit and the negative ion generating unit is arranged at a windward side along one of the separate air passages and the other one of the positive ion generating unit and the negative ion generating unit is arranged at a leeward side of the one of the positive ion generating unit and the negative ion generating unit along the other one of the separate air passages such that the positive ion generating unit and the negative ion generating unit are arranged opposite from each other; and
a flow rate in the one of the air passages through which air flows passing by the one of the positive ion generating unit and the negative ion generating unit is different from a flow rate in the other one of the air passages through which air flows passing by the other one of the positive ion generating unit and the negative ion generating unit.

2. The ion generator according to claim 1,
wherein
the partition member separates the air passage into the separate air passages such that the flow rate in the one of the separate air passages through which air flows passing by the one of the positive ion generating unit and the negative ion generating unit is larger than the flow rate in the other one of the separate air passages through which air flows passing by the other one of the positive ion generating unit and the negative ion generating unit.

3. The ion generator according to claim 1,
wherein
the flow rate in the one of the separate air passages is made different from the flow rate in the other one of the separate air passages by the partition member separating the air passage such that a sectional area of the one of the separate air passages at an inflow port side is larger than a sectional area of the other one of the separate air passages at the inflow port side.

4. The ion generator according to claim 1,
wherein
the flow rate in the one of the separate air passages is made different from the flow rate in the other one of the separate air passages by providing a resistant element on the inflow port side of the other one of the separate air passages separated by the partition member.

5. The ion generator according to claim 1,
wherein
the positive ion generating unit of the ion generating device is arranged at the windward side and the negative ion generating unit on the ion generating device is arranged at the leeward side.

6. The ion generator according to claim 1,
wherein
the flow rate in the one of the separate air passages is about 2.5 times larger than the flow rate in the other one of the separate air passages.

7. The ion generator according to claim 2,
wherein
the flow rate in the one of the separate air passages is made different from the flow rate in the other one of the separate air passages by the partition member separating the air passage such that a sectional area of the one of the separate air passages at an inflow port side is larger than a sectional area of the other one of the separate air passages at the inflow port side.

8. The ion generator according to claim 2,
wherein
the flow rate in the one of the separate air passages is made different from the flow rate in the other one of the separate air passages by providing a resistant element on the inflow port side of the other one of the separate air passages separated by the partition member.

9. The ion generator according to claim 2,
wherein
the positive ion generating unit of the ion generating device is arranged at the windward side and the negative ion generating unit on the ion generating device is arranged at the leeward side.

10. The ion generator according to claim 2,
wherein
the flow rate in the one of the separate air passages is about 2.5 times larger than the flow rate in the other one of the separate air passages.

* * * * *